(12) United States Patent
Stamler et al.

(10) Patent No.: US 7,691,907 B2
(45) Date of Patent: Apr. 6, 2010

(54) METHODS AND COMPOSITION BASED ON DISCOVERY OF METABOLISM OF NITROGLYCERIN

(75) Inventors: Jonathan S. Stamler, Chapel Hill, NC (US); Zhiqiang Chen, Durham, NC (US)

(73) Assignee: Duke University, Durham, NC (US)

( * ) Notice: Subject to any disclaimer, the term of this patent is extended or adjusted under 35 U.S.C. 154(b) by 866 days.

(21) Appl. No.: 10/508,957

(22) PCT Filed: Feb. 24, 2003

(86) PCT No.: PCT/US03/03126

§ 371 (c)(1),
(2), (4) Date: Feb. 3, 2005

(87) PCT Pub. No.: WO03/075832

PCT Pub. Date: Sep. 18, 2003

(65) Prior Publication Data

US 2005/0131063 A1    Jun. 16, 2005

Related U.S. Application Data

(60) Provisional application No. 60/361,689, filed on Mar. 6, 2002, provisional application No. 60/372,415, filed on Apr. 16, 2002, provisional application No. 60/377,204, filed on May 3, 2002.

(51) Int. Cl.
*A61K 31/095* (2006.01)
*A61K 31/045* (2006.01)

(52) U.S. Cl. ........................ 514/706; 514/738
(58) Field of Classification Search ........................ None
See application file for complete search history.

(56) References Cited

U.S. PATENT DOCUMENTS

| | | | | |
|---|---|---|---|---|
| 4,481,220 A | * | 11/1984 | Giesselmann et al. | 514/788 |
| 4,879,308 A | | 11/1989 | Alam et al. | 514/509 |
| 5,001,151 A | | 3/1991 | Alam et al. | 514/509 |
| 5,186,925 A | | 2/1993 | Cholcha | 424/43 |
| 5,489,610 A | | 2/1996 | Fung et al. | 514/506 |

FOREIGN PATENT DOCUMENTS

DE    4420102 A1    * 12/1995

OTHER PUBLICATIONS

Physicians Desk Reference Electronic Library, NITRO-DUR, Rev. Dec. 2004, copyright 1987, 2002, http://www.thomsonhc.com/pdrel/librarian, pp. 1-8.*
Physcians Desk Reference Electronic Library, Nitrolingual Pumpspray, Rev. Jun. 2006, http://www.thomsonhc.com/pdrel/librarian, pp. 1-8.*
Kennedy et al., Airway Response to Sublingual Nitroglycerin in Acute Asthma, Jul. 10, 1981, JAMA, VI. 246, No. 2, pp. 145-147.*
Murphy, Influence of redox compounds on nitrovasoliator-induced relaxations of rat coronary arteries, 1999, British Journal of Pharmacology, vol. 128, pp. 435-443.*
Laursen et al., In Vivo Nitrate Tolerance is not Associated With Reduced Bioconversion of Nitroglycerin to Nitric Oxide, 1996, Circulation, vol. 94, pp. 2241-2247; printed here p. 1-16.*
Prugin et al. Interplay between Vitamin E, Glutahione and Dihydrolipoic Acid in Protectio against Lipid Peroxidation, 1991, vol. 93, Issue 6, Abstract only (pp. 1-2).*
Getz et al., A Comparison between the Sulfhydryl Reductants Tris(2-carboxyethyl)phosphine and Dithiothreitol for Use in Protein Biochemistry, Analytical Biochemistry, vol. 23, pp. 73-80.*
Physicians' Desk Reference, NITRO-BID—CAPS and IV, 1989, Ed.43, pp. 1220-1221.*
Okuma, T., et al., "Aqueous Solution of Nitrogylcerin and Its Preparation", 00-25-76 56071046JP, Patent Appln. No. 54146011, Nippon Kayaku Co., Ltd., Copyright: (C) 1981, JPO & Japio—Abstract.
Fed. Reg. 65 (178), 55265-55266 (Sep. 13, 2000), NDA 18-672.
Information For Health Professionals—Data Sheet—Nitronal Aqueous Glyceryl trinitrate 1mg/mL injection, p. 1-6, Oct. 13, 2003.
Electronic Medicines Compendium, Merck Pharmaceuticals—Nitronal—p. 1-6, Dec. 23, 2003.
Mayer, B., "Bioactivation of Nitroglycerin—A New Piece In The Puzzle", Angew. Chem. Int. Ed., vol. 42, No. 4, 2003, pp. 388-391 : XP-002481765.
Chen, Z., et al., "Identification Of The Enzymatic Mechanism Of Nitrogylcerin Bioactivation", PNAS, vol. 99, No. 12, Jun. 11, 2002, pp. 8307-8311 : XP-002481538.

* cited by examiner

*Primary Examiner*—Frederick Krass
*Assistant Examiner*—Gigi Huang
(74) *Attorney, Agent, or Firm*—Bacon & Thomas

(57) ABSTRACT

Therapies are for treating patients in need of nitroglycerin therapy and allow increased dosage, postponement of tolerance and preconditioning, without exacerbating or causing hypotension. Methods for determining cross-tolerance, nitroglycerin effectiveness and dose are also disclosed. Composition for intravenous administration of nitroglycerin does not contain ethanol or contains less ethanol than conventional compositions.

10 Claims, 1 Drawing Sheet

US 7,691,907 B2

METHODS AND COMPOSITION BASED ON DISCOVERY OF METABOLISM OF NITROGLYCERIN

CROSS-REFERENCE TO RELATED APPLICATIONS

This application claims the benefit of U.S. Application No. 60/361,689, filed Mar. 6, 2002, of U.S. Application No. 60/372,415, filed Apr. 16, 2002, and of U.S. Application No. 60/377,204, filed May 3, 2002.

TECHNICAL FIELD

This invention is directed to therapies for patients for whom nitroglycerin (GTN) administration is indicated, screens for appropriateness of GTN for treatment, screens for cross-tolerance, and dose determination. This invention is also directed to a composition for intravenous administration of nitroglycerin.

BACKGROUND OF THE INVENTION

Nitroglycerin (glyceryl trinitrate, GTN) has been used to treat angina pectoris and congestive heart failure for over 130 years. It is generally accepted that GTN is converted in vascular smooth muscle cells to nitric oxide (NO) or an NO congener (S-nitrosothiol, SNO), which activates guanylate cyclase and this relaxes vascular smooth muscle. However, the molecular mechanism of GTN biotransformation has remained a mystery, and it is not understood why therapy with GTN is associated with nitrate tolerance (loss of clinical sensitivity to GTN) and oxidative stress (caused by GTN being an oxidant). Nitrate tolerance from GTN administration is especially evident when GTN is administered intravenously in the treatment of unstable angina and heart failure in the form of a conventional composition containing 20 mM GTN in 50% ethanol (e.g. 7 to 8 molar ethanol or over 100 times the moles of GTN) in a dosage of GTN ranging from 5 to 100 µg/min, e.g. from 20-54 µg/min, for 40 to 100 minutes. Nitrate tolerance is also noted when GTN is administered orally or topically and when isorbide dinitrate is administered orally or topically, in the treatment of angina and heart failure. Currently, nitrate tolerance is treated by increasing the dosage of nitrate administered, and this works for a while but not over the long term or for a chronic disorder (e.g., endothelulial dysfunction ensues).

GTN biotransformation has previously been found to be tissue and cell specific and to yield 1,2-glyceryl dinitrate (1,2-GDN), 1,3-glyceryl dinitrate (1,3-GDN), inorganic nitrite and NO (or SNO) in differing amounts and, ratios. Published data indicates that in vascular smooth muscle cells, 1,2-GDN is the predominant dinitrate metabolite, and either NO or SNO mediates vasodilation. Furthermore, published data indicates that the vasorelaxation-dependent formation of 1,2-GDN is reduced in GTN-tolerant blood vessels. These data suggest that the enzyme(s) generating NO bioactivity from GTN catalyzes the selective formation of 1,2-GDN (over 1,3-GDN) and that loss of this activity at least partly accounts for tolerance. Several mechanisms of vascular smooth muscle relaxation by GTN have been proposed; enzymes proposed for mediating GTN metabolism include glutathione-S-transferases, cytochrome P450 reductase, cytochrome P450, xanthine oxide reductase and an unidentified microsomal protein. However, none of these enzymes catalyzes the selective formation of 1,2-GDN or is inhibited in tolerant vessels, so none of these enzymes can be the enzyme or enzymes mediating GTN metabolism.

SUMMARY OF THE INVENTION

It has been discovered herein (data shown in background examples hereinafter) that biotransformation of GTN occurs predominantly in mitochondria through a previously unknown reductase action of the known enzyme mitochondrial aldehyde dehydrogenase (mtALDH, ALDH2) and that attenuated biotransformation of GTN by mtALDH underlies nitrate tolerance.

This discovery has led to embodiments of the invention herein directed to a method of treating a patient in need of GTN therapy, allowing inter alia increased dosage, postponement of GTN mediated tolerance and GTN preconditioning; directed to a method of increasing or stabilizing blood pressure in a hypotensive patient in need of GTN; directed to a method of preventing the occurrence of systemic hypotension in treatments with nitrate or ameliorating the presence of systemic hypotension (e.g., in light heart failure, stroke or portal hypertension; directed to treating ischemia or congestive heart failure with replacement for GTN; directed to a method of potentiating the effect of organic nitrates in a patient; directed to a method of countering loss of GTN activity in a patient; directed to a method of avoiding tolerance, mitochondrial dysfunction and atherogenic potential (predisposition to atherosclerosis because of impairment of blood vessel wall and narrowing of blood vessel because of insufficient vasodilation) in a patient in need of nitrosovasodilation (GTN therapy to dilate blood vessel(s)) comprising administrating ALDH substrate $NO_x$ donors which are not substrates for mtALDH; directed to a method of treating a patient in need of antianginal and/or preload reducing activity comprising administering mitochondria impermeable nitrate; directed to a method for determining cross-tolerance of NO-based drug and other drug; directed to a method for selecting whether GTN or other antianginal or preload reducing drug should be administered; directed to a method of determining dose of nitrate for a patient; and directed to a composition for intravenous administration of GTN whereby nitroglycerin tolerance is reversed, prevented or postponed.

We turn now to the methods of the invention.

One embodiment herein, denoted the first embodiment is directed to the method of treating a patient in need of GTN therapy, allowing inter alia increased dosage of GTN, postponement of GTN mediated tolerance and GTN preconditioning. This method comprises the steps of administering a therapeutically effective amount of GTN and of a therapeutically effective amount of an mtALDH inhibitor.

Another embodiment herein, denoted the second embodiment, is directed to the method of increasing or stabilizing blood pressure in a hypotensive patient or in a patient sensitive to GTN mediation of hypotension or in a patient where hypotension is limiting, said patient being in need of GTN therapy. This method comprises administering to said patient a therapeutically effective amount of GTN and of inhibitor of mtALDH.

Another embodiment herein, denoted the third embodiment, is directed to the method of treating ischemia or congestive heart failure in a patient in need of this. This method comprises administering to said patient an effective amount of a nitrite generator which is not GTN and is targeted to mitochondria.

Still another embodiment herein, denoted the fourth embodiment herein, is directed to the method of potentiating the effect of organic nitrates in a patient. One variation denoted the first variation of the fourth embodiment of the invention herein, is directed to a method which comprises administering to the patient a therapeutically effective amount of organic nitrate and a potentiating effective amount of a mitochondria-selective thiol or of a transgene of mtALDH which overcomes inhibition of endogenous mtALDH and/or increases nitric oxide (NO) bioavailability and/or causes decrease in GTN tolerance. Another variation denoted the second variation of the fourth embodiment of the invention herein, is directed to a method of treating a patient in need of nitroglycerin therapy comprising administering to said patient a therapeutically effective amount of nitroglycerin and a therapeutically effective amount of a dithiol and/or a therapeutically effective amount of other reductant capable of activating mtALDH.

Still another embodiment herein, denoted the fifth embodiment, is directed to a method of countering loss of GTN activity in a patient administered GTN. This method comprises administering to said patient a drug imparting NO bioactivity which does not require mtALDH for its metabolism or inhibit mtALDH in the process of bioactivation.

Still another embodiment herein, denoted the sixth embodiment, is directed to treating a patient in need of nitrosovasodilation, but avoiding tolerance, mitochondrial dysfunction and atherogenic potential. This method comprises administering to said patient a nitrosovasodilator which is not a substrate for mtALDH and preferably is a nitrosovasodilator which is a substrate for a different ALDH enzyme.

Yet another embodiment herein, denoted the seventh embodiment, is directed to a method of treating a patient in need of antianginal and/or preload reducing activity. This method comprises administering to said patient a therapeutically effective amount of a mitochondria impermeable nitrate.

Yet another embodiment herein, denoted the eighth embodiment, is directed to a method of determining cross-tolerance of nitroglycerin and other drug, e.g., other drug containing an $NO_x$ group where x is 1 or 2 or which is metabolized to produce NO bioactivity, i.e., bioactivity typically associated with NO or an NO congener. This method comprises determining whether the other drug inhibits mtALDH with inhibition indicating cross tolerance.

Yet another embodiment herein, denoted the ninth embodiment, is directed to a method for selecting whether GTN or other antianginal or other preload (the amount of blood filling the heart) reducing drug should be administered. This method comprises determining whether polymorphism exists in the mtALDH gene in the patient, and administering GTN if not, and other drug if so.

Yet another embodiment herein, denoted the tenth embodiment, is directed to a method of determining dose of nitrate for a patient. This method comprises purifying mtALDH from the patient and determining the activity of the purified mtALDH on the nitrate to determine dose that is effectively metabolized and does not cause inactivation of mtALDH.

We turn now to the composition of the invention which sometimes is referred to hereinafter as the eleventh embodiment of the invention herein. This is a composition for intravenous administration of nitroglycerin, e.g., in the treatment of unstable angina and heart failure and hypertensive emergencies, and comprises a therapeutically effective amount of nitroglycerin in a carrier and not containing compound which is or metabolizes to substrate competitive with nitroglycerin as a substrate for mitochondrial aldehyde dehydrogenase, or containing as the only carrier, one which contains no more than 25% ethanol.

mtALDH referred to in the disclosure of the invention herein is human mtALDH and is a known enzyme and is described in Vasilion, V., Chemico-Biological Interactions 129, 1-19 (2000), unless otherwise stated. However any mitochondrial mtALDH could fulfill criteria for determining inhibitor of mtALDH.

DETAILED DESCRIPTION

Figure 1:
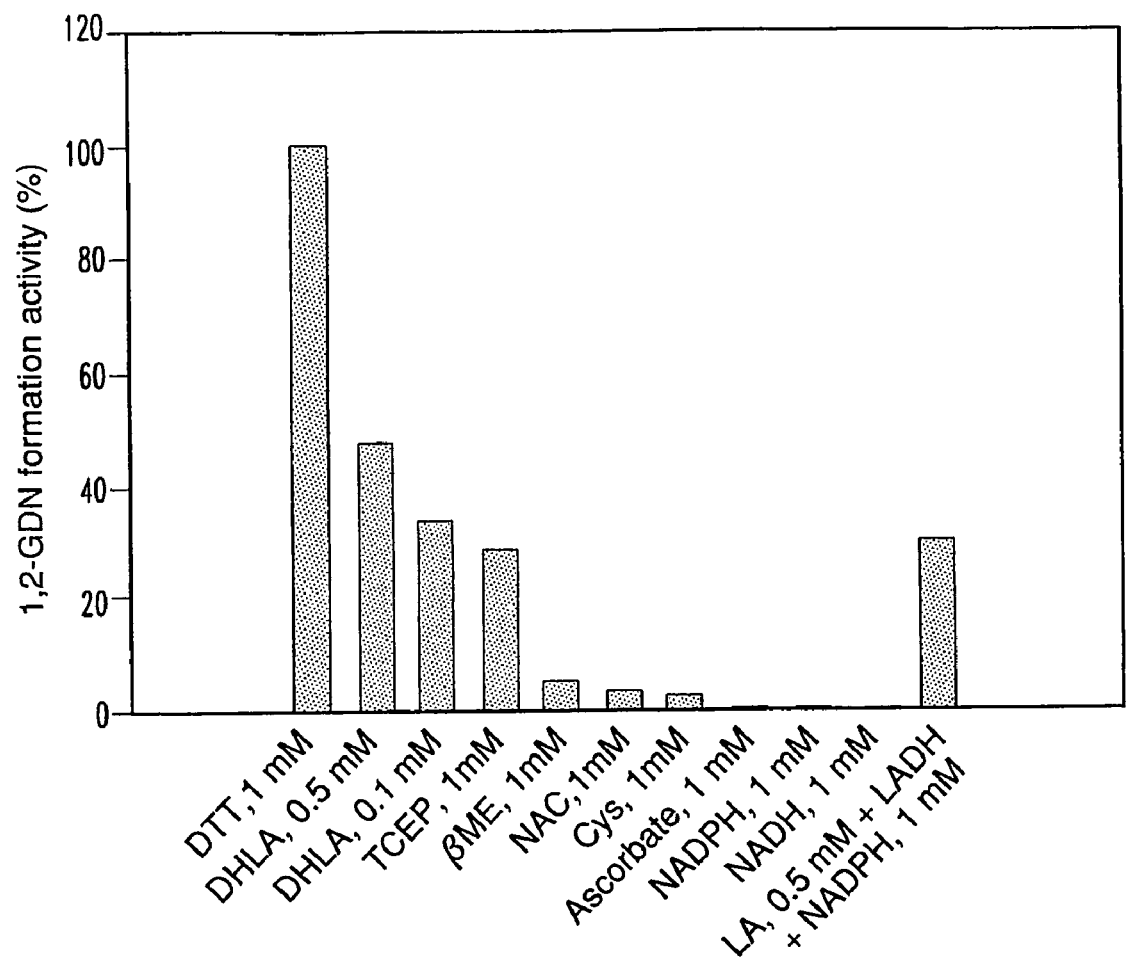
FIG. 1 is a graph showing results of Background Example 4 and particularly the percentage of 1,2-GDN produced from GTN in the presence of excess mtALDH by various agents compared to maximum possible conversion of GTN to 1,2-GDN.

We turn now to the first embodiment of the invention herein, which is a method of treating a patient in need of GTN therapy, allowing inter alia increased dosage of GTN, postponement of GTN mediated tolerance and GTN preconditioning, comprising the steps of administering a therapeutically effective amount of GTN and a therapeutically effective amount of mtALDH inhibitor.

The patient in need of GTN therapy is a patient with a disorder for which GTN therapy is now considered to be efficacious and includes a patient with an ischemic coronary syndrome (e.g., unstable angina and/or myocardial infarction), a patient with severe peripheral vascular disease, i.e., where the peripheral vascular disease limits walking of the patient, a patient who has had a transient ischemic attack, a patient who has or is at risk for a stroke, a patient with portal hypertension, a patient having a syndrome where NMDA receptor is overexcited (e.g., a neurodegenerative disorder, such as Parkinson's disease, Huntington disease, or Alzheimer's disease), asthma, rectal spasm, depression, AIDS dementia, post-operative and CABG (bypass surgery) dementia, and CNS malignancy.

The method of the first embodiment enables increasing the dosage of GTN to achieve effect without causing hypotension. This benefit is important for a patient who has or is at risk for a stroke and for a patient who has a syndrome where an NMDA receptor is overexcited or asthma, i.e., conditions where hypotension limits efficacy. Without the invention herein, the effective maximum dosage of GTN is limited by the occurrence of GTN tolerance and rarely exceeds 200 mcg/min.

As indicated above, the method of the first embodiment allows GIN preconditioning, i.e., upregulation of protective genes and enzymes that reduce injury. This function is important for patients having a disorder selected from the group consisting of ischemic coronary syndromes, severe peripheral vascular disease and transient ischemic attack.

As disclosed above, the method of the first embodiment causes postponement of GTN mediated tolerance. This occurs as a result of inhibitor protecting the mtALDH enzyme.

We turn now to the therapeutically effective amount of GTN. This ranges, for example from 10 mcg/min to 1,000 mcg/min. Doses vary greatly among patients, and therapy is titrated to blood pressure and symptoms. Administration is by intravenous route but can be topical or sublingual.

We turn now to the mtALDH inhibitor. This can be a substrate for mtALDH which is competitive with GTN, e.g., acetaldehyde, and includes agent that when administered or ingested causes increase in endogenous production of such substrate, e.g., red wine. The mtALDH inhibitors also include noncompetitive inhibitors, e.g., those which form a covalent bond at the active site of mtALDH to inhibit its activity. Noncompetitive inhibitors include cyanamide, chloral hydrate, acetaminophen, antibuse, disulfiram, and oral hypoglycemics, e.g., sulfonylurea hypoglycemic such as chloropramide, or tolazamide or glipizide.

As indicated above, the mtALDH inhibitor is administered in a therapeutically effective amount. The therapeutically effective amount is that which enables increasing the dosage of GTN, enables obtainment of GTN preconditioning and/or causes postponement of GTN mediated tolerance. The dosages for the mtALDH inhibitors can be those described in the Physician's Desk Reference for the particular inhibitor for other disorders (standard dosage), with variation with disorder treated and mtALDH inhibitor used. Normally one-tenth the standard dosage is sufficient. Exemplary cases are set forth in working examples hereinafter. The route of administration for the mtALDH inhibitor can be, for example, oral or intravenous.

We turn now to the second embodiment herein which is a method of increasing or stabilizing blood pressure in a hypotensive patient or in a patient who is sensitive to GTN mediation of hypotension or in a patient where hypotension is limiting, said patient being in need of GTN therapy, comprising administering to said patient a therapeutically effective amount of GTN and of an inhibitor of mtALDH. As used in the prior sentence, a hypotensive patient is one with a systolic blood pressure less than 90 except less than 120 for a patient with a cerebrovascular disease and less than 180 for a patient with a stroke, and hypotension means a fall in systolic blood pressure by 5 mm Hg or more.

One scenario where the second embodiment is important is when the patient has unstable angina and sepsis and cannot receive nitroglycerin for treatment of angina because of the hypotension associated with the sepsis.

Another scenario where the second embodiment is important is in a patient with a right ventricular infarct where administration of GTN is indicated but who already has hypotension or who, because of having a right ventricular infarct, is sensitive to GTN mediation of hypotension.

Other scenarios where the second embodiment is important are where GTN is being administered for a purpose at least partly unrelated to vasodilator activity and the efficacy of GTN therapy or GTN high dose therapy is limited by hypotension. This includes the case of nitrate mediated protection in preconditioning (use of nitrates to decrease the size of tissue infarction) which is at least partly unrelated to vasodilator activity and the case of a patient with or at risk for a stroke where the protective effects of nitrates are independent of their vasodilator activity. Other cases include nitrate therapy for NMDA-related disorders or asthma (where hypotension is limiting) or portal hypertension.

The mtALDH inhibitors and doses thereof and routes of administration for the second embodiment and the doses and routes of administration for GTN for the second embodiment, are the same as described above for the first embodiment herein.

The mtALDH inhibitors for this embodiment should not also block the receptor since the mtALDH enzyme mediates hypotension and the receptor mediates neuroprotection.

We turn now to the third embodiment herein which is a method of treating ischemia or congestive heart failure in a patient in need thereof comprising administering to said patient a therapeutically effective amount of a nitrite generator (an organic nitrite which produces nitrite as a metabolic product) which is not GTN and is targeted to, i.e., accesses, mitochondria.

The nitrite generators include nitro, i.e., $-NO_2$, substituted substrates for mtALDH, e.g., nitroacetaldehyde and nitrites which enter the mitochondria, e.g., ethyl nitrite as well as nitro derivatives (i.e., contains $-NO_2$ group) of lipophilic and/or cationic thiol or nitro derivatives of a lipophilic and/or cationic alcohol; this works because the mitochondrial matrix is negatively charged, and positively charged molecules are targeted there, and lipophilic molecules also are targeted to mitochondria. Thus, the use of lipophilic triphenylphosphonium cations to carry nitro group(s) provides treating agent for the third embodiment herein; thionitrobutyltriphenylphosphonium (e.g., chloride salt) is a suitable treating agent of this type.

The nitrite generators are administered in a therapeutically effective, i.e., symptom relieving amount, e.g., in a general dosage ranging from 10 mg to 1,000 mg per day, with the dosage varying with treating agent and condition treated. Exemplary dosages are given in working examples hereinafter. The route of administration is preferably intravenous, but other routes of administration, e.g., oral or topical are also useful.

We turn now to the first variation of the fourth embodiment of the invention herein, which is a method of potentiating the effect of organic nitrate in a patient administered organic nitrate, comprising administering to said patient a therapeutically effective amount of organic nitrate and also a therapeutically effective amount of a mitochondria selective thiol or of a transgene of mtALDH which overcomes inhibition of endogenous mtALDH and/or increases NO bioavailability and/or causes decrease in GTN tolerance.

mtALDH generates nitrite from nitroglycerin and the nitrite is then converted to NO bioactivity. The enzyme becomes inactivated by GTN when GTN oxidizes the enzyme. When the enzyme becomes inactivated, the result is impaired sensitivity to nitrates which is GTN tolerance. Certain thiols reverse tolerance by reducing and thereby activating the oxidized mtALDH (or other component of the mtALDH system, e.g., a component regulating level of cofactor) and by facilitating removal of $NO_2$ groups from GTN.

Transgene of mtALDH overcomes inhibition of endogenous mtALDH by providing enzymatic activity. Transgene of mtALDH increases NO bioavailability. Transgene of mtALDH causes decrease in GTN tolerance by overcoming inhibition of biotransformation.

The disorders where the first variation of the fourth embodiment herein is important include unstable coronary syndromes, including unstable angina, restenosis, heart failure, asthma and rectal spasm.

The organic nitrates for the first variation of the fourth embodiment are those which release $NO_2$ group on administration to treat the pathological disorders where such release improves symptoms of said pathological disorder. These organic nitrates include, for example, GTN, isosorbide dinitrate, nicorandil, and isosorbide mononitrate. The organic nitrates are administered in the dose normally used for the disorders treated by the routes of administration normally used, for such organic nitrates, or preferably at 30 to 60% of said dosages (i.e., a dose of 1 mcg/min to 1,000 mcg/min IV for GTN).

The mitochondria-selective thiols include, for example, amifostine and thiols which are positively charged, e.g., the thiobutyldiphenylphosphonium cation.

Where the organic nitrate is GTN, mitochondria-selective thiol can be administered to potentiate the effect of GTN by improving the efficacy or increasing the potency of GTN by reducing and thereby activating mtALDH or oxidized mtALDH and also by facilitating removal of $NO_2$ groups or by reversing GTN tolerance caused by oxidation by GTN of mtALDH by reducing the oxidized mtALDH.

The dosage for the mitochondria-selective thiol is therapeutically effective amount, i.e., a nitrate, e.g., GTN, potentiating effective amount, and can range, for example, from 1 mg/kg to 200 mg/kg and varies depending on the agent used and the disorder treated. Route of administration is preferably intravenous but can also be oral. Exemplary dosage and route of administration in treating a patient with persistent angina is given for thionitrobutylphenylphosphonium cation in working Example XIV hereinafter or, for example, is 50 mg/kg IV.

We turn now to the transgene treating agent. This supplies a functioning additional or other ALDH enzyme. Suitable transgene may be prepared by standard adenoviral vector based technology.

The transgene can be administered by infusion through a catheter inserted into a coronary artery. The transgene is administered in a GTN potentiating effective amount. Exemplary dosage and route of administration information is given in working Examples XV and XVI hereinafter.

We turn now to the second variation of the fourth embodiment of the invention herein, which is a method of treating a patient in need of nitroglycerin therapy comprising administering to said patient a therapeutically effective amount of nitroglycerin and a therapeutically effective amount of a dithiol and/or a therapeutically effective amount of other reductant capable of activating mtALDH.

It is stated in the art that monothiols such as N-acetylcysteine, which raise levels of glutathione, can reverse tolerance, but it is now appreciated that monothiols potentiate GTN effect independent of reversing tolerance. As indicated above, nitrolglycerin tolerance occurs because mtALDH enzyme is inactivated by GTN oxidizing the enzyme and/or components of the enzyme system required to maintain enzyme activity. Inasmuch as monothiols do not reverse this inactivation, monothiols cannot reverse tolerance.

We turn now to definition of terms used above in describing the second variation of the fourth embodiment of the invention herein.

The term "reductant" is used herein to mean reducing agent.

The term "capable of activating mtALDH" is used herein to mean capable of reducing oxidized mtALDH so the enzyme can catalyze conversion of GTN to 1,2-GDN. Reductants that do not cause at least 20% 1,2-GDN formation in the procedure of Background Example 4 hereinafter, are not capable of activating mtALH.

We turn now in detail to the second variation of the fourth embodiment of the invention herein.

The disorders of the patients in need of nitroglycerin therapy for the second variation of the fourth embodiment of the invention herein, include unstable coronary syndromes including unstable angina, restenosis, heart failure, portal hypertension, asthma and rectal spasm.

In the second variation of the fourth embodiment of the invention herein, the nitroglycerin is administered in a dose used for the disorders treated, by the routes of administration normally used, or preferably at 30 to 60% of said dosages (e.g., a dose of 1 mcg/min to 1,000 mcg/min IV). For angina the dosage is a pain ameliorating amount. For restenosis, the dosage is a heart vessel relaxing amount. For heart failure, the amount is a blood flow increase causing amount. For asthma, the amount is an airway relaxing amount. For rectal spasm, the amount is a spasm ameliorating amount. For portal hypertension, it is a portal pressure lowering amount.

We turn now to the dithiols. The dithiols are preferably mitochondria selective. The term "mitochondria selective" is used herein to mean ability to access mitochondria more readily than other cell components. A preferred dithiol for use herein is dihydrolipoic acid which is mitochondria selective and also is physiological in that it is a chemical made in the body. Dihydrolipoic acid for use herein is available commercially and can be purchased in pharmaceutically pure form.

We turn now to the other reductants capable of activating mtALDH. A preferred reductant capable of activating mtALDH for use herein which is not a dithiol is tris(2-carboxyethylphosphine). Tris(2-carboxyethylphosphine) is available commercially and can be purchased in pharmaceutically pure form.

The dosage for the thiols and the other reductants for the second variation of the fourth embodiment of the invention herein is a therapeutically effective amount, that is a nitroglycerin tolerance reversing, postponing or preventing amount, and can range, for example, from 1 mg/kg to 200 mg/kg and varies depending on the agent used and the disorder treated. Route of administration is preferably intravenous but also can be oral. Exemplary dosage and route of administration in treating a patient with persistent angina are given for dihydrolipoic acid in working example XXXII hereinafter, and are, for example, 50 mg/kg IV. Exemplary dosage and route of administration for unstable angina are given for tris (2-carboxyethylphosphine) in working example XXXIII hereinafter and are, for example, 1 gm infused over 30 minutes.

We turn now to the fifth embodiment herein which is directed to a method of countering loss of GTN activity, i.e., reversing GTN tolerance, in a patient administered GTN comprising administering to said patient a drug imparting NO bioactivity (e.g., nanomolar amounts of NO bioactivity) that does not require mtALDH for its metabolism. Currently, loss of GTN activity is countered only by increasing dosage of GTN.

The patients for this embodiment are those, for example, in need of antianginal or preload (load on the right side of the heart) reducing activity. Patients in need of preload reducing activity include patients with heart failure, angina or myocardial infarction.

Drugs, for example, which include nitroso group or which are mononitrites, thionitrites, thionitrates, can be assessed for use in the fifth embodiment herein by activity in aortic ling bioassays as described in Stamler, J. S., et al., PNAS 89, 444-448 (1992).

Suitable drugs include S-nitrosoglutathione, glycerol mononitrite, glycerol thionitrite and glycerol thionitrate. Dosage is a therapeutically effective amount, i.e., an amount which relieves one or more symptoms and generally ranges from nanomolar to micromolar final concentrations in the blood or airway but varies within this range depending on the drug administered and disorder treated. Route of administration usually is intravenous but can also be oral or topical. Working examples XX and XXI set forth hereinafter show specific dosages and routes of administration for S-nitrosoglutathione and glycerol thionitrite.

We turn now to the sixth embodiment of the invention herein which is directed to a method of treating a patient in need of nitrosovasodilation (blood vessel dilation from an NO donor (compound that is able to transfer $NO^+$, $NO^-$, $NO^*$, $NO_2^+$ or $NO_2^-$ to biological molecules or mediate such transfer)) but avoiding tolerance, mitochondrial dysfunction and atherogenic potential, comprising administering to the patient a nitrosovasodilator which is not a substrate for human mtALDH and/or is a substrate for a different human ALDH, i.e., aldehyde dehydrogenase enzyme, which has been or will be determined by sequence homology to human mtALDH.

Tolerance as used in the previous sentence means loss of nitrosovasodilation activity. Mitochondrial dysfunction as used in this paragraph means causing impairment of blood vessel wall. Atherogenic potential as used in this paragraph means predisposes to atherosclerosis because of impairment of blood vessel wall and narrowing of blood vessel because of insufficient vasodilation. Nitrosovasodilator as used in this paragraph means compound that is able to transfer $NO^+$, $NO^-$, $NO^*$, $NO_2^+$ or $NO_2^-$ to biological molecules or mediate such transfer, to obtain blood vessel dilation.

The patients for the sixth embodiment herein include, for example, patients in need of antianginal or preload (load on the right side of the heart) reducing activity, e.g., patients with the angina or heart failure.

Treating agents for the sixth embodiment herein include 2-glycerol mononitrite and amyl nitrate which are not a substrate for human mtALDH and not a substrate for other ALDH enzyme.

Treating agents for the sixth embodiment herein also include those which are a substrate for human ALDH enzyme which is not mtALDH, and contain $NO_2$ moiety. We turn to these treating agent substrates.

One class of these substrates are $NO_2$ derivatives of 13-cis retinol. These are substrates for the ALDH ekes, human ALDH1A1, ALDH1A2 and ALDH1A3.

13-cis-retinal has the structure:

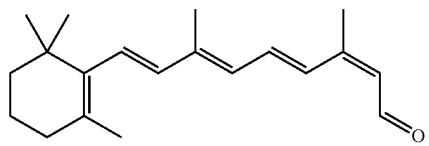

$NO_2$ derivatives of 13-cis-retinal useful herein include:

(1)
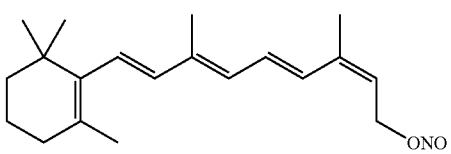

(2)
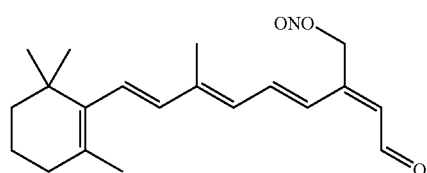

(3)
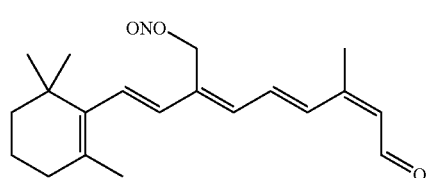

(4)
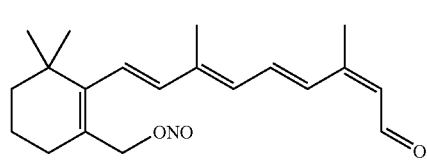

-continued (5)
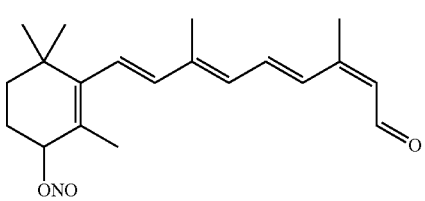

(6)
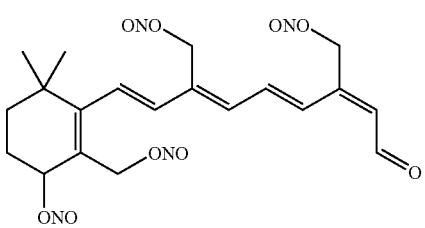

Compounds (1)-(6) are prepared from 13-cis-retinal by allylic oxidation, separation and o-nitrosation.

A member of another class of these substrates is mega-NO which is a substrate for the ALDH enzyme, human ALDH1A1.

Another class of these substrates are $NO_2$ derivatives of acetaldehyde. These are substrates for the ALDH enzymes human ALDH1A1, ALDH1B 1 as well as for human mtALDH.

Acetaldehyde has the structure:

$NO_2$ derivatives of acetaldehyde useful herein include (7)
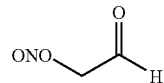

(8)
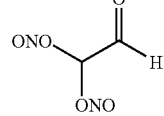

(9)
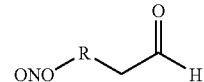

In structure (9), R is $C_1$-$C_6$ alkyl or other organic backbone.

Compound (7) can be prepared from hydroxyacetaldehyde (glycolaldehyde dimer) by o-nitrosation. Compound (8) can be prepared from glyoxal by partial hydration and o-nitrosation. Compound (9) can be prepared from acetaldehyde by nucleophilic attack of the enolate on an appropriate substrate and o-nitrosation.

Another class of these substrates are $NO_2$ derivatives of folic acid. These are substrates for the ALDH enzyme human ALDH1L1.

Folic acid has the structure:

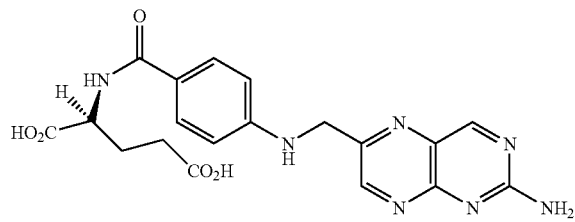

NO$_2$ derivatives of folic acid useful herein include:

(10)

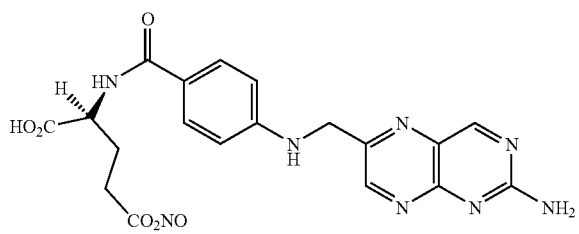

(11)

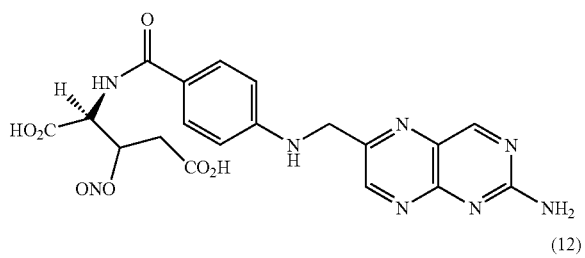

(12)

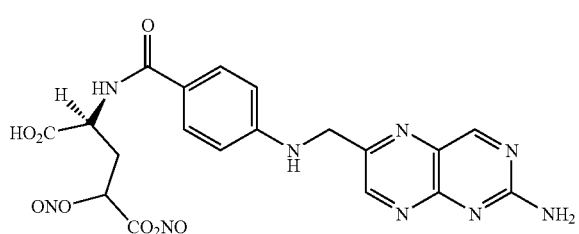

(13)

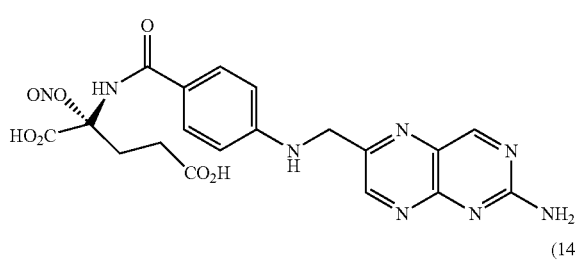

(14)

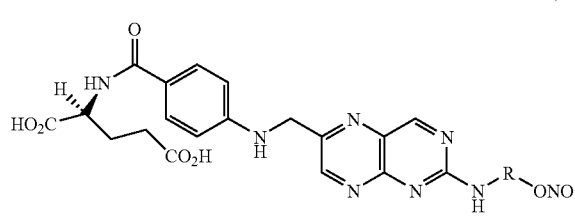

(15)

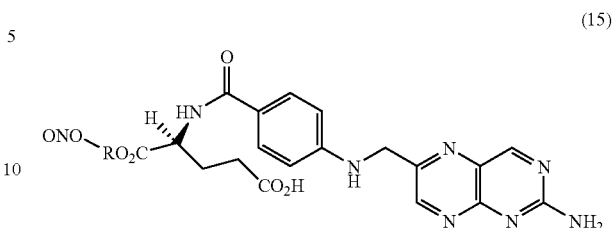

(16)

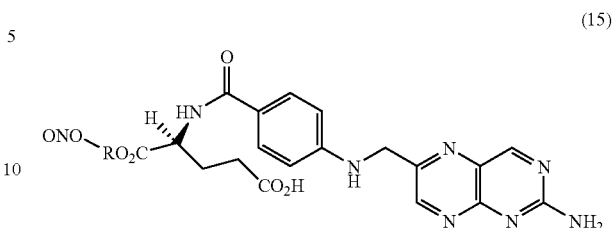

In structures (15) and (16), R can be C$_1$-C$_6$ alky or other organic backbone.

Compounds (10)-(16) can be prepared from folic acid by esterification, alpha-hydroxylation, and, and o-nitrosation for —ONO compounds, and by o-nitrosation for —CO$_2$NO compounds, with necessary protection/deprotection.

Another class of these substrates are NO$_2$ derivatives of aromatic aldehydes. These are substrates for the ALDH enzyme human ALDH3A1.

Benzaldehyde has the structure:

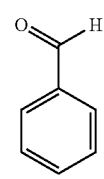

NO$_2$ derivatives of benzaldehyde useful herein include (17)

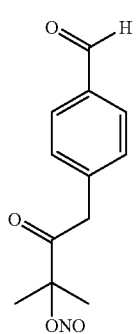

-continued

(18)
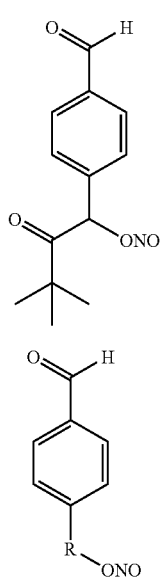

(19)
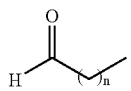

In structure (19), R can be $C_1$-$C_6$ alkyl or other organic backbone.

Compounds (17)-(19) can be made from commercially available benzaldehyde derivatives by alpha-hydroxylation and/or o-nitrosation.

Still another class of these substrates are $NO_2$ derivatives of fatty aldehydes. These are substrates for the ALDH exhale human ALDH3A2.

Fatty aldehydes have the structures

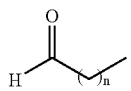 and 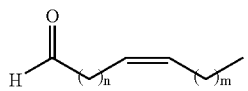

where n ranges from 0 to 34 and m ranges from 0 to 34.

$NO_2$ derivatives of fatty aldehydes useful herein include

(20)
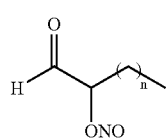

(21)
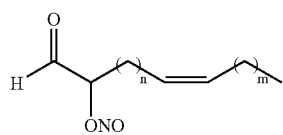

In structures (20) and (21), n ranges from 0 to 34 and m ranges from 0 to 34.

Compounds (20) and (21) can be made from fatty acids by reduction, alpha-hydroxylation, and o-nitrosation, with necessary protection/deprotection.

Still another class of these substrates are $NO_2$ derivatives of succinic semialdehyde. These are substrates for the ALDH enzyme human ALDH5A1.

Succinic semialdehyde has the structure:

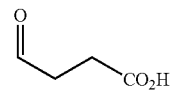

$NO_2$ derivatives of succinic semialdehyde useful herein include:

(22)
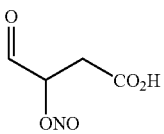

(23)
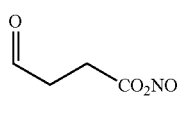

(24)
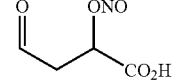

(25)
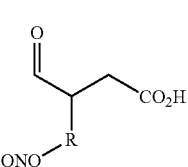

(26)
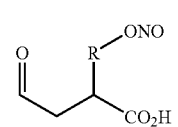

In structures (25) and (26), R can be $C_1$-$C_6$ alkyl or other organic backbone.

Compounds (22)-(26) can be made by the appropriate combination of the following: esterification, alpha-hydroxylation, nucleophilic attack by the enolate, saponification, and o-nitrosation, with necessary protection/deprotection.

Yet another class of these substrates are $NO_2$ derivatives of L-glutamic acid, semi-aldehyde. These are substrates for the ALDH enzyme human ALDH4A1.

L-Glutamic acid, semi-aldehyde has the structure:

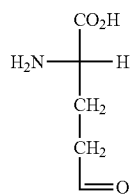

$NO_2$ derivatives of L-glutamic acid, semi-aldehyde useful herein include

(27) 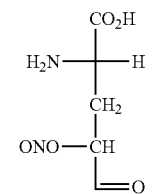

(28) 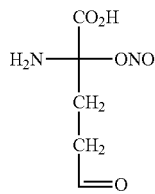

(29) 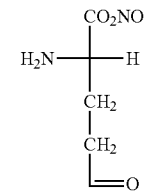

(30) 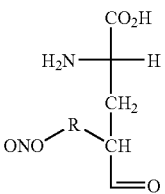

In structure (30), R can be $C_1$-$C_6$ alkyl or other organic backbone.

Compounds (27)-(30) can be made by from L-glutamic acid by the appropriate combination of the following: protection esterification, alpha-hydroxylation, nucleophilic attack of the enolate, and o-nitrosation, and deprotection.

Yet another class of these substrates are $NO_2$ derivatives of methyl malonate semialdehyde. These are substrates for the ALDH enzyme human ALDH6A1.

Methyl malonate semialdehyde has the structure

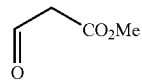

$NO_2$ derivatives of methyl malonate semialdehyde useful herein include

(31) 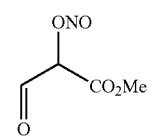

(32) 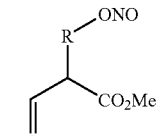

(33) 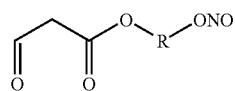

In structures (32) and (33), R can be $C_1$-$C_6$ alkyl or other organic backbone.

Compounds (31)-(33) can be prepared by appropriate oxidation or reduction of malonate derivatives and o-nitrosation, with protection/deprotection as needed.

Yet another class of these substrates are $NO_2$ derivatives of amino aldehydes. These are substrates for the ALDH enzyme human ALDH9A1.

Amino aldehyde substrates for ALDH9A1 have the structure:

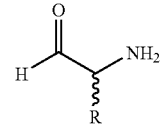

where R can be $C_1$-$C_6$ alkyl or other organic moiety.

$NO_2$ derivatives of amino aldehydes useful herein include:

(34)

(35)

In (34) and (35), R can be $C_1$-$C_6$ alkyl or other organic moiety.

Compounds (34) and (35) can be made by alpha-hydroxylation and o-nitrosation of protected/deprotected derivatives.

The dosage for the treating agent for the sixth embodiment is a therapeutically effective, e.g., symptom relieving, amount, and can range from nanograms to milligrams per day with variation within the range for the various treating agents and the disorders treated. Route of administration can be oral or intravenous or topical. The route of administration for amyl nitrate and 2-glycerol mononitrite is preferably oral.

$NO_2$ is cleaved from (1)-(35) by ALDH enzyme because it is a reactive group and is displaced by biological nucleophile.

The second human ALDH enzyme in the mitochondria (i.e., besides mtALDH) is human ALDH1B1 and it metabolizes aliphatic aldehydes. NO$_2$ containing substrates for it described above are a preferred treating agent for the sixth embodiment herein.

We turn now to the seventh embodiment herein which is a method for treating a patient in need of antianginal and/or preload reducing activity, comprising administering to said patient a therapeutically effective amount of mitochondria impermeable nitrate or nitrite.

The disorders treated in the seventh embodiment are the same as the disorders mentioned above for patients in need of antianginal or preload reducing activity.

The treating agent for the seventh embodiment herein is a nitrate which is mitochondria impermeable. These can be nitrates with a negative charge as structures with a negative charge do not access the mitochondria. Treating agents useful herein in the seventh embodiment include the following:

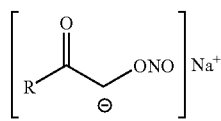  (36)

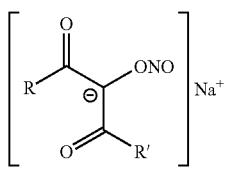  (37)

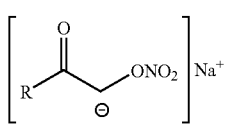  (38)

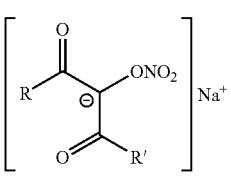  (39)

wherein R is $C_1$-$C_6$ alkyl or other organic moiety and R' is $C_1$-$C_6$ alkyl or other organic moiety.

Compounds (36)-(39) can be made by deprotonation of the o-nitrosated or o-nitrated substrate with necessary protection/deprotection.

As indicated above, the compounds are administered in a therapeutically effective amount which for the seventh embodiment is an angina or preload reducing amount. Dosage generally ranges from 10 to 1,000 mg/day with variation with this range occurring depending on drug administered and disorder treated. Route of administration can be, for example, intravenous, oral or topical.

We turn now to the eighth embodiment herein which is directed to a method of determining cross-tolerance of nitroglycerin and other drug comprising assaying to determine whether the other drug inhibits mammalian mtALDH with inhibition indicating cross-tolerance.

Certain classes of drugs such as sulfonylurea hypoglycemics, chloral hydrate and acetaminophen inhibit human mtALDH activity and are thus here discovered to be contraindicated in a patient taking organic nitrate esters for the treatment of acute ischemic syndromes and congestive heart failure.

Furthermore, if a nitrosothiol, for example, inhibits human mtALDH, it would attenuate the therapeutic effect of nitroglycerin and vice-versa. Thus, an assay to determine cross-tolerance of nitroglycerin and other drug which contains an $NO_x$ group where x is 1 or 2 or which is metabolized to produce NO bioactivity (activity associated with NO, e.g., vasodilation) would be useful to select a drug to complement the NO bioactivity of GTN.

The assay for the eighth embodiment can be any which determines whether the other drug inhibits mtALDH under the physiological or pathophysiological conditions which are present. The mtALDH for the assay is preferably human mtALDH for the most accurate results, but can be other mtALDH which has the conserved sequences of human mtALDH and at least 30% homology. For example, the mtALDH from mouse macrophage RAW 264.7 cells, the purification of which is described in Background Example 1 hereinafter, can be used. An exemplary assay is described in Kebay, W., et al., PNAS 94, 1675-1679 (1997). The effect of drug (at 1 nM-1 μM concentration) on enzyme activity is assessed. In a preferred assay, aldehyde dehydrogenase activity is monitored at room temperature by following NADH formation at 340 nm in an assay mixture (1 ml) containing 100 mM tris-HCl pH8.5, 1 mM NAD$^+$, 1 mM propionaldehyde. In the preferred embodiment, human, the assay can be done on blood cells isolated from the patient.

We turn now to the ninth embodiment herein which is a method of selecting between GTN and other antianginal or preload reducing drug for administering to a patient in need of antianginal and/or preload reducing activity, comprising determining whether polymorphism (variation in gene that alters enzyme activity) exists in the mtALDH gene of the patient, and administering GTN if not, and other drug, if so.

The patients in need of antianginal and/or preload reducing activity are described above.

We turn now to the reason why the assay of the ninth embodiment is important. There can be a polymorphism in the mtALDH gene that is linked to ethanol metabolism. If this polymorphism is present, GTN is inactive in the patient.

If polymorphism indicating that GTN will be ineffective is found, a nitrate ester different from GTN should be administered instead, e.g., pentaerythritol tetrathionitrate, or pentaerythritol tetranitrate.

The mtALDH genotyping to determine the polymorphism can be carried out, for example, by standard genetic methods using blood cells.

We turn now to the tenth embodiment herein which is a method of determining dose of nitrate for a patient comprising purifying mtALDH from the patient and determining the activity of the purified mtALDH on the nitrate to determine dose that is effectively metabolized and does not cause inactivation of mtALDH.

The mtALDH is preferably purified from erythrocyte or other blood cell of the patient. This can be carried out, for example, using the same steps as in Background Example 1. Enzyme activity is determinable as described for the eighth embodiment above.

The assay of the tenth embodiment is especially useful when it is proposed to give GTN prophylactically to prevent an episode of angina. In such case, there would be no basis for knowing whether the GTN would be effectively metabolized or whether the dose is too high (as measured by inactivation of the mtALDH).

If the assay shows the purified mtALDH from the patient effectively metabolizes GTN, then GTN would be given.

If the assay shows the purified mtALDH from the patient does not effectively metabolize GTN, then other nitrate ester, e.g., pentaerythritol tetranitrate, or pentaerythritol tetrathionitrate would be given if testing determined it was effectively metabolized by the purified mtALDH.

The determination of activity of the purified mtALDH is also important as a predictor in respect to tolerance, i.e., so as to give a dose that would be effective for at least an acute condition without the causing of GTN tolerance.

We turn now to the eleventh embodiment of the invention herein.

As indicated above, GTN is conventionally administered intravenously in the treatment of unstable angina and heart failure and in hypertensive emergencies, typically in a dosage ranging from 5 to 100 μg/min, e.g., from 20 to 54 μg/min, for 40 to 100 minutes, in the form of a composition containing 20 mM GTN in 50% ethanol (e.g., 7 to 8 molar ethanol or over 100 times the moles of GTN).

The discovery of the mechanism for biotransformation of GTN being by reductase action of mtALDH on GTN in the course of making the invention herein, and the known action of alcohol dehydrogenase in metabolizing ethanol with the production of acetaldehyde (See page 624 of Goodman & Gilman's The Pharmaceutical Basis of Therapeutics, Eds. Hardiman, J., G, et al, McGraw-Hill, New York, 10th edition, 2001), and the known action of acetaldehyde as a substrate for mtALDH, and the known effect of GTN infusion producing side effects like those caused by disulfiram in those who drink alcohol (indicating based on the discovery mentioned above, competition for the action of mtALDH) and the showing in Background Example 2 hereinafter that acetaldehyde inhibits the action of mtALDH so far as GTN metabolism is concerned, lead to the conclusion that the ethanol present in a composition for intravenous administration of GTN will interfere with the effectiveness of the GTN as a result of the acetaldehyde metabolism product of ethanol being a competitive substrate for the same enzyme as metabolizes GTN. This leads to the further conclusion that insofar as nitrate tolerance is measured by loss of effectiveness of GTN, ethanol which is present in compositions for intravenous administration of GTN, reduces the effectiveness of GTN and thereby contributes to the development of nitrate tolerance.

The eleventh embodiment of the invention herein addresses the contribution of ethanol, in compositions for intravenous administration of GTN, to reduction of GTN effectiveness and is directed to a composition for intravenous administration of GTN, said composition comprising a therapeutically effective amount of GTN in a carrier and either not containing compound which is or metabolizes to substrate competitive with the GTN as a substrate for mtALDH, e.g., not containing ethanol, or containing as the only carrier, one which contains a reduced amount of ethanol compared to conventional compositions for intravenous administration of GTN, e.g., no more than 25% ethanol.

In a case where the composition does not contain any of the ethanol which is conventionally present as one of the carrier ingredients for intravenous administration of GTN, the carrier for the composition comprises, for example, vehicle selected from the group consisting of an alcohol different from ethanol, e.g., methanol, propanol, isopropanol or butanol, a glycol, glycerol, saline and phosphate buffered saline. The alcohols, glycols and glycerol are typically in the form of 40-60% aqueous solutions. Saline can be used as pure saline.

The use of methanol and ethylene glycol are limited to non toxic amounts. Since nitroglycerin is not very soluble in water (1 gm in 800 ml compared to 1 gram in 4 ml ethanol) and sparingly soluble in glycerol, use of pure saline, phosphate buffered saline and glycerol as or in carriers for the GTN, involves administration of larger amounts of GTN-containing compositions, containing these, but this can be acceptable because the concentration of GTN that is active is still at least 1000 times lower than its solubility. Preferred carrier constituents to replace ethanol are propylene glycol and isopropanol, with 40-60% propylene glycol or isopropanol in water being more preferred and 50% propylene glycol in water being very preferred.

We turn now to the cases where the composition contains some ethanol but a reduced amount of ethanol compared to conventional compositions for intravenous administration of GTN. In one case the composition should contain at least 100% less ethanol than the conventional composition, i.e., the carrier should contain no more than 25% ethanol. In another case the composition should contain at least 10 fold lower amount of ethanol than the conventional composition, i.e., the carrier should contain no more than 5% ethanol. Applicable compositions include 2 to 30 nM GTN in 0.1 to 25%, e.g., 0.5% to 25%, e.g., 1 to 25%, e.g., 5-10%, ethanol.

As indicated above, a therapeutically effective amount of GTN is included in a composition. This amount is limited by the toxicity of the carrier and the solubility of GTN in the carrier. For compositions where the carrier is 50% propylene glycol in water or 50% isopropanol in water, the GTN is present, for example, at a concentration ranging from 2 to 30 mM.

As with conventional compositions for intravenous administration of GTN, the compositions herein are useful for treatment of unstable angina, heart failure and hypertensive emergencies and may be used to treat myocardial infarction, by intravenous administration. The administration rate depends on the solubility of GIN in the carrier and the toxicity of the carrier. For 40-60% propylene glycol or isopropanol in water as the carrier, application rates of 1-100 μg/min, e.g., 20-54 μg/min, of nitroglycerin, for 40 minutes to 2 days, are applicable. Use of lower application rates, e.g., 1-5 μg/min have the advantage of not causing nitrate tolerance or postponing it compared to conventional cases.

The following Background Examples 1-3 are basis for the discovery underlying the inventive embodiments herein, that biotransformation of GTN occurs predominantly in mitochondria through a previously unknown reductase action of mtALDH and that the attenuated biotransformation of GTN by mtALDH underlies nitrate tolerance.

The following Background Example 4 is basis for the discovery that administration of dithiols and other reductants capable of activating mtALDH can reverse, postpone or prevent nitroglycerin tolerance.

BACKGROUND EXAMPLE 1

Purification of mtALDH from Cell Sample Generating Mainly 1,2-GDN from GTN

Different animal tissues and cell hues were screened by monitoring 1,2-GDN formation by thin layer chromatography from physiological (submicromolar) amounts of GTN. It was found that mouse macrophage RAW264.7 cells (obtained from ATCC) resemble vascular smooth muscle cells in generating 1,2-GDN as a product of GTN metabolism and, following homogenization by sonication, the enzyme activity was predominantly in the 100,000 g supernatant.

Enzyme producing 1,2-GDN from GTN was isolated from mouse macrophage RAW264.7 cells by the procedure described below.

During protein purification, the assay mixtures (1 ml samples) contained 100 mM KPi, pH7.5, 0.5 mM EDTA, 1 mM NADH, 1 mM NADPH, 0.1 or 1 µM [$^{14}$C]GTN and protein sample from column fractions. After incubation at 37° C. for 10 to 30 minutes, the reaction was stopped (by adding dry ice) and GTN and its metabolites were extracted by 3×4 ml ether, the ether phase was combined and the solvent was evaporated by a stream of nitrogen. The final volume was controlled to less than 100 µl in ethanol for subsequent thin layer chromatography (TLC) separation and liquid scintillation spectrometry counting, i.e., (TLC-LSS), to determine amount of [$^{14}$C]1,2-GDN, to select samples with enzymatic activity (i.e., 1,2-GDN producing activity).

Enzyme purification was carried out as follows: Mouse macrophage RAW 264.7 cells were homogenized in a 30 mM phosphate buffer (KPi), pH 7.5, containing 1 mM dithiothreitol (DTT), 0.5 mM EDTA and protease inhibitors (1:200 dilution). The 100,000 g supernatant was loaded onto a DEAE-cellulose column and the flow through fractions which contained the enzyme activity were pooled and concentrated. After three-fold dilution with cold water, the pooled flow through fractions were loaded onto a Q-sepharose column and the activity was eluted by a phosphate gradient from 10 mM to 150 mM, pH 7.5; the active fractions were pooled and solid potassium chloride (KCl) was added to 1.25 M. The sample was then loaded on a Butyl-Sepharose column. The enzymatic activity was eluted by decreasing the salt concentration. The concentrated active fractions were diluted and loaded onto a hydroxyapatite column. After washing the column with 10 mM KPi/0.4 M KCl the enzyme was eluted by a phosphate gradient from 10 mM KPi to 150 mM KPi pH7.5.

Results after each step for GTN reductase purification from the mouse macrophage RAW264.7 cells is set forth in Table 1 below.

TABLE 1

| Step | Total Unit (nmole/hr) | Total Protein (mg) | Specific Activity (nmole/hr/mg) | Yield Percent | Fold Purification |
|---|---|---|---|---|---|
| 100,000 g supernatant | 837.4 | 2265 | 0.37 | 100 | 1 |
| DEAE-Cellulose | 756.0 | 345 | 2.19 | 90.3 | 5.9 |
| Q-Sepharose | 528.5 | 123 | 4.29 | 63.1 | 11.6 |
| Butyl-Sepharose | 205.4 | 10.9 | 18.81 | 24.5 | 50.8 |
| Hydroxyapatite | 120.9 | 3.6 | 33.36 | 14.4 | 90.2 |

At the end of the procedure, the protein had been purified to near homogeneity (90 fold), with a 14.4% overall yield; its estimated molecular weight on SDS gel is about 53 kDa. N-terminal sequence of 30 amino acid residues was obtained by Edman degradation and matched exactly with mouse mitochondria aldehyde dehydrogenase. To confirm that the isolated enzyme is located in the mitochondria and responsible for production of 1,2-GDN, preparations of mitochondria isolated from RAW 264.7 cells were assayed and found to generate 1,2-GDN from GTN (0.29 nmole/hr/mg, 1 mM NADH/NADPH) whereas mitochondria-free supernatant had no residual activity.

The purified enzyme catalyzed the formation of 1,2-GDN and nitrite ($NO_2^-$) from GTN. Specifically, the rates of 1,2-GDN formation were linear with physiological GTN concentrations in the range of 0.1 to 10 µM, whereas 1,3-GDN was below detection limits, and nitrite was generated in stoichiometric amounts; the product ratio of 1,2-GDN/nitrite (0.83±0.14, n=3) was similar to that of 1,2-GDN/$NO_x$ (nitrite plus nitrate) (0.73±0.05, n=3). Thus, the overall reaction can be expressed as:

$$GTN \rightarrow 1,2\text{-}GDN + NO_2^-$$

It was found that the purified enzyme could only catalyze 1,2-GDN formation when dithiol, e.g., dithiothreitol (DTT) or lipoic acid, was added. Further, the catalytic activity was lost upon removal of DTT by dialysis and could be fully restored by addition of DTT but not by glutathione (monothiol).

The specific conversion of GTN to 1,2-GDN and dependence on thiol cofactor (as reductant) make mtALDH a compelling candidate as being the enzymatic system responsible for catalyzing the bioactivation of GTN in the human vasculature. This hypothesis was tested in the experiments of Background Examples 2 and 3, leading to the conclusion that mtALDH is the enzymatic system responsible for the bioactivation of GTN in the human vasculature.

BACKGROUND EXAMPLE 2

Effect of mtALDH Inhibitors and Competitive Substrate on GTN Caused Relaxation of Vascular Smooth Muscle, 1,2-GDN Production and cGMP Production, In Vitro, and on GTN Caused Relaxation In Vivo New Zealand white rabbits (2.5-3 kg) were sacrificed by carbon monoxide inhalation. Thoracic aorta were removed and cleaned of fat and connecting tissue, and were cut into 3 mm rings. The rings were mounted under two grams of resting tension in tissue baths (25 ml) filled with Krebs solution at 37° C. The Krebs solution contains (mM): NaCl (118), KCl (4.8), $MgSO_4$ (1.2), $KH_2PO_4$ (1.2), $CaCl_2$ (2.5), $NaHCO_3$ (25), glucose (11), pH 7.4. The solution was bubbled with 20% $O_2$, 5% $CO_2$ and balance $N_2$. Changes in isometric tension were recorded with Stratham transducers and a Gross polygraph. (Phenylephrine 1-10 µM) was used to produce initial tension. Vasorelaxation activities of GTN and sodium nitroprusside (SNP) were measured for cumulative addition of GTN and SNP. Relaxation curves were obtained of percent relaxation versus log [GTN](M) and log [SNP](M). Preincubation of the rings with the mtALDH inhibitors chloral hydrate and cyanamide or with the competitive substrate acetaldehyde, produced a rightward shift in the GTN relaxation curves. The $EC_{50}$ values for GTN induced relaxation were as follows: choral hydrate control, 14.5±5.9 nM, +chloral hydrate, 122.9±63.5 nM (P<0.01); cyanamide control, 15.8±6.0 nM, +cyanamide, 76.9±5.3 nM (P<0.01); acetaldehyde control, 13.1±5.7 nM, +acetaldehyde, 58.2±14.3 nM (P<0.01). The $EC_{50}$ was increased 8.9, 4.9 and 4.4 fold respectively, and the rightward shifts were dependent on inhibitor/competitive substrate concentration. By contrast, preincubation with the mtALDH inhibitors did not attenuate relaxation induced by the nitrosovasodilator SNP, by NO solutions or by verpamil which works through an NO-independent mechanism. The results suggest a specific inhibition of the organic nitrate ester reductase activity in the arterial vasculature.

Testing was carried out to confirm that 1,2-GDN generated in the aorta rings was reduced. For measurement of 1,2-GDN, the rings were blotted and weighed before incubation in the bath chamber for one hour in Krebs solution. Assaying was conducted in test tubes where the rings were incubated with the inhibitors/competitive substrate in Krebs solution for 20 minutes before the addition of 1 µM GTN whereupon the mixture was kept at 37° C. for 5 more minutes. The extraction and following TLC-LSS analysis are the same as described in Background Example 1. Buffer control (Krebs buffer plus GTN) and nonspecific biotransformation (heat inactivated rings plus GTN) experiments were also performed. 1,2-GDN formation activities were reported as subtraction of that of buffer control. The testing showed 1,2-GDN generation in the aorta rings was reduced by 1 mM chloral hydrate, 1 mM; cyanamide and 1 mM: acetaldehydes to 27.6%, 56.9% and 52.5% of control activity respectively.

Testing was also carried out to determine whether the GTN reductase inhibitors and competitive substrate also significantly decreased cGMP accumulation in the aortic rings. Chloral hydrate and acetaldehyde, 1 μM for 1 minute, completely blocked the increase in cGMP produced by GTN and cyanamide (100 μM-10 nM) reduced the cGMP increase by 46%.

As a further test of the physiological role of mtALDH in bioactivation of GTN, the effect of the mtALDH inhibitors cyanamide and chloral hydrate (at a dose lower than used in clinical practice) on the systemic effects of GTN infusion in anesthetized rabbits was assessed. In this testing, New Zealand white rabbits (2.5-3 kg) were anesthetized with isoflurane (15%). The carotid artery and jugular vein were isolated via cut down and cannulated. The arterial blood pressure was monitored continuously using Viggio Spectramed pressure transducer attached to a Gould recorder. GTN and other drugs was infused via the jugular vein: mtALDH inhibitors (~5 mM) were infused intravenously 20 minutes prior to initiating studies with GTN. Both inhibitors significantly attenuated the hypotensive effects of GTN, whereas they had little or no effect on SNP (i.e., NO dependent) or adenosine (i.e., NO independent mediated hypotension).

BACKGROUND EXAMPLE 3

Effect of GTN Tolerance on GTN Caused Relaxation of Vascular Smooth Muscle 1,2-GDN Production and cGMP Production, In Vitro Rabbit aortic ring assays were carried out as in Background Example 2 except that the rings were made GTN tolerant by treatment with 0.3 mM GTN for 30 minutes and no mtALDH inhibitor/competitive substrate was present. Vasorelaxation activities of GTN and SNP were measured for cumulative additions of GTN and SNP. Relaxation curves were obtained of percent relaxation versus log [GTN](M) and log [SNP](M). The $EC_{50}$ values for GTN relaxation for GTN tolerant control and for GTN tolerant were respectively 22.6±9.2 nM and 3757.5±2048.5 ($p<0.05$). By contrast, no effect was found on SNP-induced relaxations on GTN tolerant rings compared to control.

Testing in GTN tolerant aortic rings for 1,2-GDN formation was carried out by the procedure of Background Example 2. The testing showed reductase activity as measured by 1,2-GDN formation decreased 60.4% in GTN-tolerant rings compared to control.

Testing was carried out to compare cGMP production from GTN treatment of GTN tolerant aortic rings compared to control. The testing showed cGMP accumulation was abolished in the GTN tolerant rings whereas cGMP accumulation was obtained in control rings.

In addition, testing showed that activity of mtALDH in partially purified preparations of GTN tolerant aortic rings, was inhibited.

Conclusions from Background Examples 1-3 mtALDH is the enzyme responsible for catalyzing the bioactivation of GTN in the human vasculature and its inactivation underlies the occurrence of GTN tolerance.

GTN has relaxing effects independent of cyclic GMP.

BACKGROUND EXAMPLE 4

Determination that Dithiols and Other Reductants Activate mtALDH but not Monothiols mtALDH isolated from mouse macrophage RAW 264.7 as described in Background Example 1 above, was used.

The test mixture was 1 mM GTN in ethanol vehicle together with an excess of said mtALDH The GTN caused oxidation of mtALDH within a few minutes. Various compounds were then added and incubation was carried out at 37° C. for 10-30 minutes. The various compounds added were dithiothreitol (DTT), 1 mM; dihydrolipoic acid (DHLA), 0.5 mM; dihydrolipoic acid (DHLA), 0.1 mM; tris(carboxyethylphosine), denoted TCEP, 1 mM; 2-mercaptoethanol (βME), 1 mM; n-acetylcysteine (NAC), 1 mM; cysteine (CyS), 1 mM; ascorbate, 1 mM; NADPH, 1 mM; NADH 1 mM; and lipoic acid (LA), 0.5 mM+15 mcg lipoamidedehydrogenase (LADH), an enzyme which converts lipoic acid to dihydrolipoic acid, +NADPH (necessary for functioning of LADH), 1 mM.

The results are shown in FIG. 1. As shown in FIG. 1, the best activators of mtALDH to cause conversion of GTN to 1,2-GDN, from among the compounds tested, were DTT, DHLA and TCEP. Of those DHLA and TCEP are preferred therapeutic agents to be administered together with GTN to reverse, postpone or prevent nitroglycerin tolerance from occurring in a patient.

The embodiments of the invention are illustrated by the following working examples.

EXAMPLE I

A 70-year-old white male with an evolving stoke and angina is begun on nitroglycerin IV at a dose of 0.6 mg per hour per day (or 0.1 μg/kg/min). The blood pressure dropped from 160 systolic to 120 mm Hg and the patient was then given chloral hydrate 50 mg P.O. Blood pressure rose to 160 systolic and the nitroglycerin dose was then increased to 0.3 μg/kg/min.

EXAMPLE II

A 29-year-old white male with AIDS dementia is given the nitroglycerin patch (Nitro-bid), 2 inches of paste q 8 hours, but develops a headache and orthostatic hypotension. He is begun on Tylenol 1 gram q 4 hours with resolution of both the headache and symptoms of orthostasis.

EXAMPLE III

A 69-year-old white male with Parkinson's disease is given nitroglycerin in conjunction with antibuse (500 mg P.O.) and the dose of nitroglycerin was increased progressively from 2 mg per day to 24 mg per day without headache or symptomatic hypotension and the patient's symptoms improve, whereas the patient had been previously intolerant to these higher doses.

EXAMPLE IV

A 60-year-old white male with unstable angina is given 2 glasses of red wine to increase endogenous production of acetaldehyde and thereby allow nitroglycerin to be started at a dose of 1 mg per hour per day with relief of symptoms, whereas previous attempts to gradually raise the dose of nitroglycerin to achieve these levels induced tolerance.

EXAMPLE V

A 55-year-old white male presents with elevated levels of troponim and an unstable coronary syndrome. No EKG changes are observed and the patient's pain resolves in the Emergency Room with sublingual nitroglycerin. The patient is then begun on IV nitroglycerin (20 μg/min) and chloral hydrate (250 mg q 6 hr). The following day the patient has a myocardial infarction as evidenced by EKG changes and a CPK rise. Angiography shows complete occlusion of the left anterior descending coronary artery, but left ventricular function is largely preserved, consistent with a preconditioning effect of drugs.

EXAMPLE VI

A similar patient presents with unstable angina and is given IV nitroglycerin, 0.2 μg/kg/min, and glipizide (20 mg/day). The patient suffers a myocardial infarction the following day with preservation of left ventricular function.

EXAMPLE VII

A 63-year-old white male with unstable angina and sepsis cannot receive nitroglycerin because of hypotension and his angina remains inadequately treated. The patient is begun on (disulfiram 500 mg P.O.) and then IV nitroglycerin is started (2.0 μg/min) with no effect on blood pressure. The patient's angina resolves.

EXAMPLE VIII

A 53-year-old white male with hypocholesterolemia presents with an inferior myocardial infarction and hypotension. Right sided EKG leads show the presence of a right ventricular infarct and the patient is begun on chloral hydrate 1 gm P.O. followed by IV nitroglycerin at 0.1 μg/kg/min with resolution of symptoms, and the patient's blood pressure improves.

EXAMPLE IX

A 65-year-old white male presents with a left-sided deficit and au evolving stroke. His blood pressure is 180 systolic which is the lower limit that is desirable in a patient with a stroke. He is begun on a combination of intravenous nitroglycerin and 1 gram of chloral hydrate. The nitroglycerin dose is increased from 20 μg per minute to 100 μg per minute without a decline in blood pressure. The left sided deficit resolves.

EXAMPLE X

A 62-year-old presents with unstable angina and the electrocardiogram shows light ventricular ischemia. He is begun on 1 gram of chloral hydrate and intravenous nitroglycerin at 20 μg per minute without a fall in blood pressure. The troponin level increases indicating a myocardial infarction but the echocardiogram shows preservation of both light ventricular and left ventricular function, and the blood pressure remains stable at 110 mm of mercury. Electrocardiographic evidence of ischemia resolves.

EXAMPLE XI

A 73-year-old white male presents with a left hemispheral stroke and is begun on intravenous nitroglycerin which drops systolic blood pressure from 200 systolic to 140 mm of mercury systolic. The patient is given intravenous acetaldehyde titrated to achieve circulating concentrations of 1-10 μM, thereby normalizing blood pressure. The treatment prevents the stroke from progressing.

EXAMPLE XII

A 73-year-old white female with unstable angina becomes tolerant to IV nitroglycerin as evidenced by requiring increasing doses and loss of antianginal efficacy. A study of ALDH activity is done in the patient's red blood cells and the enzyme was found to be inhibited. The patient is began on IV ethyl nitrite, 0.1 μg/kg/mm, with a fall in blood pressure from 160 systolic to 120 mm Hg. Anginal symptoms resolve.

EXAMPLE XIII

A 73-year-old with angina and congestive heart failure becomes tolerant to nitrates as evidenced by dyspnea and leg swelling despite increasing doses of the ding from 0.1 to 0.5 μg/kg/min over 24 hours. The patient is begun on nitroacetaldehyde (which is targeted to mitochondria) at 0.1 mg/kg/min with relief of dyspnea.

EXAMPLE XIV

A 56-year-old white male with progressive tolerance to intravenous nitroglycerin has persistent angina. He is begun on an IV infusion of thionitrobutyltriphenylphosphonium chloride, at 15 mg/kg q 6 hrs with relief of symptoms and enhanced sensitivity to nitroglycerin. The dose of nitroglycerin was then reduced in half.

EXAMPLE XV

A 56-year-old with unstable angina on IV nitroglycerin develops tolerance over 48 hours as evidenced by recurrent chest pains despite increasing doses of drug. He is given an intracoronary infusion of ALDH transgene ($10^7$ PFU) with relief of symptoms.

EXAMPLE XVI

A 62 year-old white male develops unstable angina four weeks following placement of a stent in the left anterior coronary artery and restenosis is documented angiographically. The patient is begun on intravenous nitroglycerin but symptoms persist. The patient is given an intracoronary infusion of ALDH2 transgene with relief of angina. The lesion is reopened and restenosis does not recur.

EXAMPLE XVII

A 27-year-old white female with asthma is given 2 inches of nitropaste with no improvement in symptoms. She is then begun on chloral hydrate 1 gm q 6 hrs and the nitroglycerin dose is increased 5-fold with improvement in wheezing and shortness of breath. No limiting hypotension is noted.

EXAMPLE XVIII

A 52-year-old white male with rectal spasm has nitroglycerin ointment placed topically but symptoms persist. Increasing the dose of nitroglycerin causes the blood pressure to drop from 120 to 100 mm Hg limiting therapy. The patient is therefore begun on Tylenol 1 gm q 6 hrs and the nitroglycerin dose is increased three-fold with relief of symptoms.

EXAMPLE XVIII A

A 20-year-old female presents with status asmaticus and is intubated. She receives inhaled nitroglycerin (3 cc of a 100 mM solution) with slight improvement but the effect is lost over the following 24 hours. She is then begun on amifostine nebulized (3 cc of a 100 mM solution) with a 12% improvement in FEV 1.

EXAMPLE XVIII B

A 42-year-old male with rectal spasm is given topical nitroglycerin with no effect. A solution of 100 mM amifostine is added with resolution rectal pain.

EXAMPLE XIX

A 57-year-old white male with heart failure remains short of breath despite increasing doses of nitroglycerin. The patient is begun on 0.1 µg/kg/min of S-nitrosoglutathione with improvement of dyspnea and relief of angina.

EXAMPLE XX

A 69-year-old white male with a myocardial infarction is tolerant to IV infusions of nitroglycerin and develops recurrent chest pain on a nitrate free interval. The patient is begun on 0.1 µg/kg/min of glycerol thionitrite with immediate relief of symptoms.

EXAMPLE XXI

A 62-year-old white male with heart failure is unresponsive to increasing doses of nitroglycerin. He is begun on amyl nitrate 0.6 mg per hour per day with improvement in dyspnea and symptoms of fatigue.

EXAMPLE XXII

A 72-year-old white male presents with unstable angina and is begun on intravenous nitroglycerin, leading to tolerance over the following 48 hours. The patient is then begun on mega-NO (13-cis-retinal derivative) at 10 µg/min in place of nitroglycerin with relief of ischemia.

EXAMPLE XXII A

A 60-year-old white female presents with unstable angina which recurs despite increasing doses of nitroglycerin. The patient is begun on mega-NO with relief of symptoms and nitroglycerin is discontinued.

EXAMPLE XXIII

A 42-year-old on isosorbide dinitrate for therapy develops progressive atherosclerosis, but decreasing the dose exacerbates his symptoms of congestive heart failure. The patient is begun on 10 mg/day of 2 glycerol mononitrite with relief of symptoms. Angiography the following year shows no progression of atherosclerosis.

EXAMPLE XXIV

A 70-year-old white male with congestive heart failure and mycardial ischemia is begun on 20 µg unit of 10 µ/min of mitochondria impermeable nitrate (Compound (36) set forth above). The preload is reduced and the patient's ischemia resolves.

EXAMPLE XXV

A 42-year-old is begun on intravenous nitroglycerin to treat congestive heart failure. Over the following day tolerance evolves, evidenced by increase in shortness of breath at higher doses, and the patient is switched to Imdur, which is less efficacious. To determine if tolerance has reversed, the blood is sampled for mtALDH activity. Once the activity is normalized, IV nitroglycerin is restarted. The functionality of Imdur after administration of nitroglycerin and of nitroglycerin after administration of Imdur shows no cross-tolerance between nitroglycerin and Imdur, i.e., that nitroglycerin does not prevent the effect of Imdur and vice versa.

EXAMPLE XXVI

A 67-year-old Chinese male develops angina on IV nitroglycerin 0.1 µg/kg/min. An assessment of mtALDH genotype is made on a sample of the patient's blood showing that the mtALDH enzyme has low activity. Nitroglycerin is substituted by S-nitrosoglutathione 0.1 µg/kg/min with relief of symptoms.

EXAMPLE XXVII

A 72-year-old with unstable angina is given IV nitroglycerin at 0.1 µg/kg/min. Measurement of mtALDH genotype shows that enzyme activity is low. Nitroglycerin is stopped and the patient is started on pentaerythritol tetranitrate 60 mg P.O. T. I. D.

EXAMPLE XXVIII

A 57-year-old with heart failure has an assessment of mtALDH activity and mtALDH genotype made from red blood cell and lymphocyte, respectively, to determine responsiveness to nitroglycerin. The patient is found to have normal enzyme activity and is begun on hydralazine and nitroglycerin in a standard regimen for heart failure.

EXAMPLE XXIX

A 62-year-old white male with congestive heart failure has an assessment of mtALDH genotype, and mtALDH activity, as done in the previous example, but in this case the enzyme is shown to be low activity (less than half normal) and the patient is given pentaerythritol tetrathionitrate 60 mg 3×/day P.O. in place of nitroglycerin. The patient is also started on Captropril 15 mg T.I.D.

EXAMPLE XXX

A 42-year-old with congestive heart failure is given intravenous nitroglycerin and tolerance evolves over the following 24 hours. To best titrate the dose of nitroglycerin, the blood is assayed for mtALDH activity at various doses and the patient is then maintained at the highest dose which does not induce enzyme inhibition. Nitroglycerin is then administered continuously for four days without tolerance.

EXAMPLE XXXI

A 47-year-old with congestive heart failure is begun on nitroglycerin and red blood cell mtALDH activity is assayed intermittently to ensure that tolerance does not evolve.

EXAMPLE XXXII

A 70-year old patient with angina becomes nitroglycerin tolerant. Treatment with 50 mg/kg dihydrolipoic acid, IV, every 6 hours, reverses tolerance and maintains mtALDH activity. Continued infusions of the DHLA prevent tolerance from recurring.

EXAMPLE XXXIII

A 67-year old patient with unstable angina becomes tolerant to infusion of nitroglycerin and develops angina. One gram of tris(carboxyethylphosphine), denoted TCEP, is infused over 30 minutes and tolerance is reversed and angina resolves.

EXAMPLE XXXIV

A composition is made up containing GTN (20 mM) in 50% aqueous propylene glycol The composition may be administered intravenously at 5-100 µg/min for 40 to 100 minutes to treat a patent with an acute attack of unstable angina, with heart failure, with a hypertensive emergency or with a myocardial infarction.

EXAMPLE XXXV

A composition is made up containing GTN (20 mM) in 50% aqueous isopropanol. The composition may be administered intravenously at 5-100 µg/min for 40 to 100 minutes to treat a patient with an acute attach of unstable angina, with heart failure, with a hypertensive emergency or with a myocardial infarction.

EXAMPLE XXXVI

A composition is made up containing GTN (4 mM) in pure saline. The composition may be administered, at 1-10 µg/min for 1 to 2 days to treat a patient with an acute attack of unstable angina, with heart failure, with a hypertensive emergency or with a myocardial infarction.

EXAMPLE XXXVII

A composition is made up containing GTN (5 mM) in 5% ethanol. The composition may be administered at 1-10 µg/min for 1 to 2 days to treat a patient with an acute attack of unstable angina, with heart failure, with a hypertensive emergency or with a myocardial infarction.

EXAMPLE XXXVIII

A 60-year old alcoholic with cirrhosis and portal hypertension is given topical nitrates to alleviate ascites and becomes dizzy and hypotensive. The patient is given one gram of chloral hydrate orally and blood pressure is restored.

Variations

Many variations will be obvious to those skilled in the art. Therefore, the invention is defined by the scope of the claims.

What is claimed is:

1. A method of activating inactivated mtALDH in a patient who has received nitroglycerin therapy and has become nitroglycerin tolerant so the patient no longer responds to nitroglycerin comprising administering inactivated mtALDH activating effective amount of agent selected from the group consisting of dihydrolipoic acid, dithiothreitol and tris(2-carboxyethylphosphine).

2. The method of claim 1 where the patient is affected with a disorder selected from the group consisting of angina, restenosis, heart failure, portal hypertension, asthma and rectal spasm.

3. The method of claim 2 where the patient is affected with angina.

4. The method of claim 3 where the agent is dihydrolipoic acid.

5. The method of claim 3 where the agent is dithiothreitol.

6. The method of claim 3 where the agent is tris(2-carboxyethylphosphine).

7. The method of claim 1 where the agent is dihydrolipoic acid.

8. The method of claim 1 where the agent is dithiothreitol.

9. The method of claim 1 where the agent is tris(2-carboxyethylphosphine).

10. A method for restoring clinical sensitivity to nitroglycerin to a patient who has lost sensitivity to nitroglycerin so that the patient no longer responds to nitroglycerin comprising administering to the patient a nitroglycerin sensitivity restoring amount of dihydrolipoic acid, dithiothreitol or tris (2-carboxyethylphosphine).

* * * * *